(12) United States Patent
Kaufmann et al.

(10) Patent No.: US 8,749,788 B2
(45) Date of Patent: Jun. 10, 2014

(54) OPTOELECTRONIC APPARATUS FOR GAS ANALYSIS AND METHOD

(75) Inventors: Jürgen Kaufmann, Denzlingen (DE); Frank Nuber, Emmendingen (DE); Michael Overdick, Emmendingen (DE); Rolf Schiffler, Kenzingen (DE)

(73) Assignee: Sick AG, Waldkirch (DE)

( * ) Notice: Subject to any disclaimer, the term of this patent is extended or adjusted under 35 U.S.C. 154(b) by 139 days.

(21) Appl. No.: 13/118,618

(22) Filed: May 31, 2011

(65) Prior Publication Data

US 2012/0002205 A1 Jan. 5, 2012

(30) Foreign Application Priority Data

Jul. 5, 2010 (EP) .................................. 10168397

(51) Int. Cl.
*G01N 21/59* (2006.01)
*H01J 49/04* (2006.01)
*G01N 21/15* (2006.01)
*G01N 21/35* (2014.01)
*G01N 21/67* (2006.01)

(52) U.S. Cl.
CPC ............ *G01N 21/15* (2013.01); *G01N 21/3504* (2013.01); *G01N 21/67* (2013.01); *H01J 49/0422* (2013.01)
USPC .......................................... 356/437; 250/288

(58) Field of Classification Search
CPC ... G01N 21/15; G01N 21/3504; G01N 21/67; H01J 49/0422
USPC .......... 356/432–444; 250/288, 286, 287, 340, 250/343, 324; 436/52, 173, 153
See application file for complete search history.

(56) References Cited

U.S. PATENT DOCUMENTS 3,626,179 A * 12/1971 Cohen ........................... 250/282
4,205,969 A     6/1980 Matsumoto
(Continued)

FOREIGN PATENT DOCUMENTS

CA   2 704 114 A1   5/2009
DE   88 10 485 U1  12/1988
(Continued)

OTHER PUBLICATIONS

Extended European Search Report issued Sep. 14, 2010, in priority European Application No. 10168397.7.
(Continued)

*Primary Examiner* — Sang Nguyen
(74) *Attorney, Agent, or Firm* — Nath, Goldberg & Meyer; Jerald L. Meyer

(57) ABSTRACT

The invention relates to an improved optoelectronic apparatus for optical gas analysis by means of which the interfering influence of the particles contained in the gas is reduced with regard to the intended measurement. For this purpose the optoelectronic apparatus in accordance with the invention has a light transmitter and a light receiver which define an optical measurement path including a measurement volume between one another. The received signals of the light receiver can be evaluated in an evaluation unit, to ultimately obtain the desired information therefrom, for example, the concentration of a specific gas content. In accordance with the invention an ionizer is further provided which is arranged upstream of the optical measurement path. The ionizer causes an ionization of the undesirable particles, i.e. e.g. the dust particles, smoke particles or such like aerosols so that the ionized particles can be deflected by electric fields or also magnetic fields by means of an ion acceleration apparatus. In this respect the ion acceleration apparatus and/or its electromagnetic fields is/are aligned such that the generated ions experience a deflection to be able to flow past the measurement volume.

10 Claims, 3 Drawing Sheets

(56) References Cited

U.S. PATENT DOCUMENTS

Figure 1:
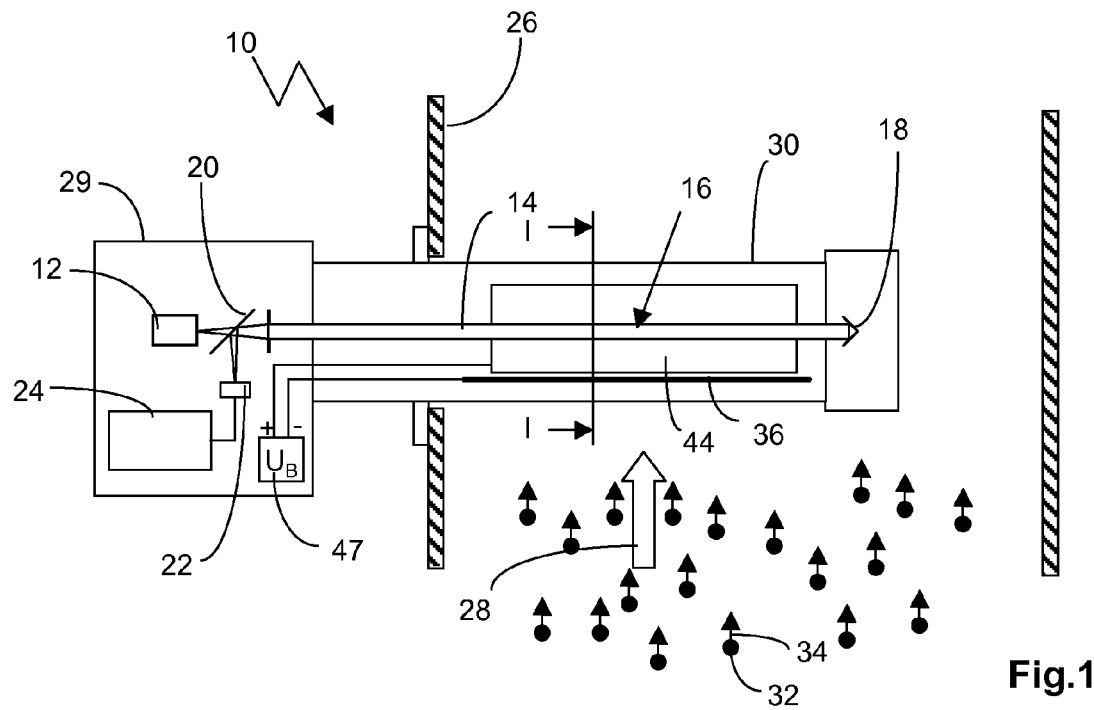

| | | | |
|---|---|---|---|
| 5,808,299 A * | 9/1998 | Syage | 250/288 |
| 6,333,632 B1 * | 12/2001 | Yang et al. | 324/464 |
| 6,407,382 B1 * | 6/2002 | Spangler | 250/286 |
| 7,091,481 B2 * | 8/2006 | Miller et al. | 250/288 |
| 7,416,902 B2 * | 8/2008 | Pletcher et al. | 436/174 |
| 7,547,878 B2 * | 6/2009 | Schultz et al. | 250/282 |
| 7,605,389 B1 | 10/2009 | Doughty | |
| 7,733,490 B2 * | 6/2010 | Goodwin et al. | 356/436 |
| 7,816,646 B1 * | 10/2010 | Willoughby et al. | 250/288 |
| 8,044,343 B2 * | 10/2011 | Arii et al. | 250/281 |
| 8,071,938 B2 * | 12/2011 | Guharay | 250/287 |
| 2003/0015045 A1 * | 1/2003 | Yoshida et al. | 73/865.5 |
| 2009/0189064 A1 * | 7/2009 | Miller et al. | 250/282 |
| 2011/0243802 A1 * | 10/2011 | Ringheim et al. | 422/186.04 |

FOREIGN PATENT DOCUMENTS

| | | |
|---|---|---|
| DE | 38 01 262 A1 | 7/1989 |
| DE | 100 11 531 A1 | 9/2001 |
| JP | 2009115654 A | 5/2009 |
| KR | 20060113669 A | 11/2006 |

OTHER PUBLICATIONS

Office Action issued by the Korean Patent Office, Oct. 30, 2012.

* cited by examiner

OPTOELECTRONIC APPARATUS FOR GAS ANALYSIS AND METHOD

The invention relates to an optoelectronic apparatus for optical gas analysis as well as to a method for optical analysis of the gas.

Such apparatuses are, for example, optical spectrometers, range of vision sensors, in-situ gas analyzers, tunnel sensors and such like. Specific gas constituents, for example, hydrogen sulfide, carbon monoxide, SO2, NH3, NO, NO2, HCl, HF or such like are measured with such apparatuses by means of optical transmission or light scattering. In this respect the concentration of these gas constituents is measured for the most part.

Fields of applications are, for example, emission measurements of industrial plants, in which the content of certain molecular compounds in the exhaust gases have to be monitored. Frequently the gas flows, to which the optoelectronic apparatuses are subjected to measure the desired gas constituents, are characterized by high particle loads, such as, for example, smoke, dust or other aerosols. These high particle loads cause a large light absorption and/or a high light scattering which strongly hampers the measurement itself or renders the measurement impossible. As such, for example, hydrogen sulfide has a very large absorption as has, for example, ultra-fine dust. It can then no longer be differentiated whether the absorption is brought about by the hydrogen sulfide or by the dust.

Electric filters are principally known to purify gases. Such an electric filter is utilized, for example, in accordance with DE 38 01 262 A1 to protect a ceramic measurement chip of an air mass flow meter in an engine intake passage from contamination with such particles. From DE 100 11 531 A1 an apparatus for probe extraction for the extracted gas analysis of coke oven crude gas and other contaminated gases is known in which the gas is deviated from the coke oven tube, is filtered a plurality of times, cooled and is also treated by means of an electric filter to finally be able to guide it in purified form to a gas analyzer. Disadvantages of such extractive gas analysis techniques are the change of the filter in time, the requirement of cleaning the filter or the filter exchange, the undesired modification of the medium by the gas extraction path, the filter or the filtrate.

On the other hand, in-situ gas analysis frequently occurs then when an additional treatment of the gas is not required and is not desired, i.e. the gas should be measured "directly".

Starting from this prior art, it is the object of the invention to provide an improved optoelectronic apparatus for optical gas analysis by means of which the interfering influences of the particles present in the medium on the designated measurement is reduced.

For an optoelectronic apparatus for gas analysis in a gas flow the object is satisfied by an apparatus having the features of claim 1 and a method having the features of claim 8.

An optoelectronic apparatus in accordance with the invention for optical gas analysis in a gas flow has a light transmitter and a light receiver which define an optical measurement path including a measurement volume between one another. The received signals of the light receiver are evaluatable in an evaluation unit, to finally obtain the desired information therefrom, for example the concentration of a specific gas constituent. In accordance with the invention an ionizer is further provided which is arranged upstream of the optical measurement path. The ionizer causes an ionization of the inferring particles, i.e. for example, the dust particles, smoke particles or similar aerosols so that the ionized particles can be deflected by electric fields or also magnetic fields by means of an ion acceleration apparatus. In this respect the ion acceleration apparatus and/or its electromagnetic fields is/are designed such that the generated ions experience a deflection so that they can flow past the measurement volume.

The ionizer preferably works with electromagnetic fields so that the actual measurement component, for example, a certain molecule is not ionized by the ionizer, but only the interfering particles are ionized. Thus, the interfering particles can be kept out of the measurement volume—at least a large part thereof—by means of the ion acceleration apparatus so that the measurement itself is not interfered with or is even only enabled thereby. An additional treatment of the dust loaded gas flow is thus still provided in accordance with the invention despite of the in-situ gas analysis.

The ionizer is preferably configured as an electric ionizer so that the ionization takes place due to electric field effects. In this respect the ionizer is preferably designed as a discharge electrode of an electric filter and the ion acceleration apparatus is formed by the discharge electrode and a collector electrode of the electric filter. In this way a corona discharge can be formed around the discharge electrode which leads to the ionization of the particles in the gas which can then be deflected in the direction of the collector electrode. Typical field strength amount to e.g. 5 kV/cm. Arrangements of such kinds of electric filters are generally known and well-established so that a dimensioning is simplified.

Alternatively it is principally also plausible that the ions are deflected by magnetic fields.

It is provided, in an improvement of invention, that the collector electrode is arranged at least laterally of the measurement volume when viewed in the flow direction to deflect the ionized particles such that they—at least for the most part—flow past the measurement volume. The ionization and the deflection viewed in the flow direction, should at least occur in front of the measurement volume. For this reason the collector electrode must be arranged at least laterally of the measurement volume.

The probability of ionization can be increased on using a plurality of discharge electrodes, wherein the plurality of discharge electrodes are advantageously arranged upstream of the optical measurement path.

When the optical measurement volume is located in a region without flow, the discharge electrode of the electric filter is arranged in the measurement volume and a collector electrode is arranged outside of the volume in a further embodiment of the invention. Then the ionized particles are namely accelerated out of the measurement volume into the direction of the collector electrode, i.e. they are deflected.

Frequently this is the case when the measurement volume is arranged in a mechanical filter, preferably in a filter frit. In this case the electric filter is preferably integrated into the filter frit.

In this respect the discharge electrode is advantageously at least partly arranged centrally in the measurement volume and the collector electrode is arranged at the inner surface of the mechanical filter or is formed by the filter itself.

A method in accordance with the invention for optical analysis of a gas in a gas flow includes the following steps:
- transmission of a light beam into a measurement volume penetrating the gas flow,
- receiving the light beam with a receiver and generating received signals,
- evaluating the received signals,
- ionizing particles in the gas flow in an electric field and deflecting the ionized particles with the electric field so that these experience a deflection in the direction away from the measurement volume so as to be able to flow past the measurement volume.

In an embodiment of the method in accordance with the invention the field strength is modulated and the received signals are evaluated under the consideration of the modulation. The electric field applied to the ion acceleration apparatus must thus not necessarily be static, but can also be dynamically modulated, in particular be modulated periodically. The overall concentration of the particles in the medium can also be measured or at least be partly estimated by the evaluation of the received signals in dependence on the modulation for periodic modulation. Even a statement on the particle size distribution can be derived from the received signal for a poly-disperse particle size distribution on selection of suitable modulation frequency of the modulation wave form and a sufficiently fine time resolution of the optical measurement channel. This is based on the fact that different sized particles present in the electric field have different rates of mobility and for this reason are accelerated to different degrees from the optical measurement volume or into the optical measurement volume as this is generally known in an analogous manner from the O'Brien theory.

Figure 2:
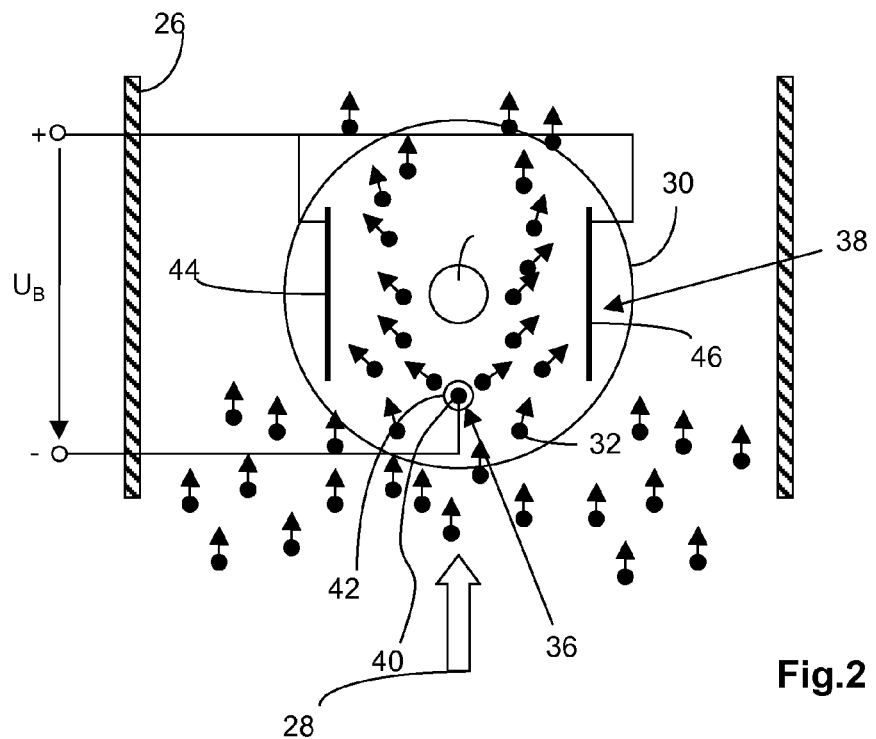
Figure 3:
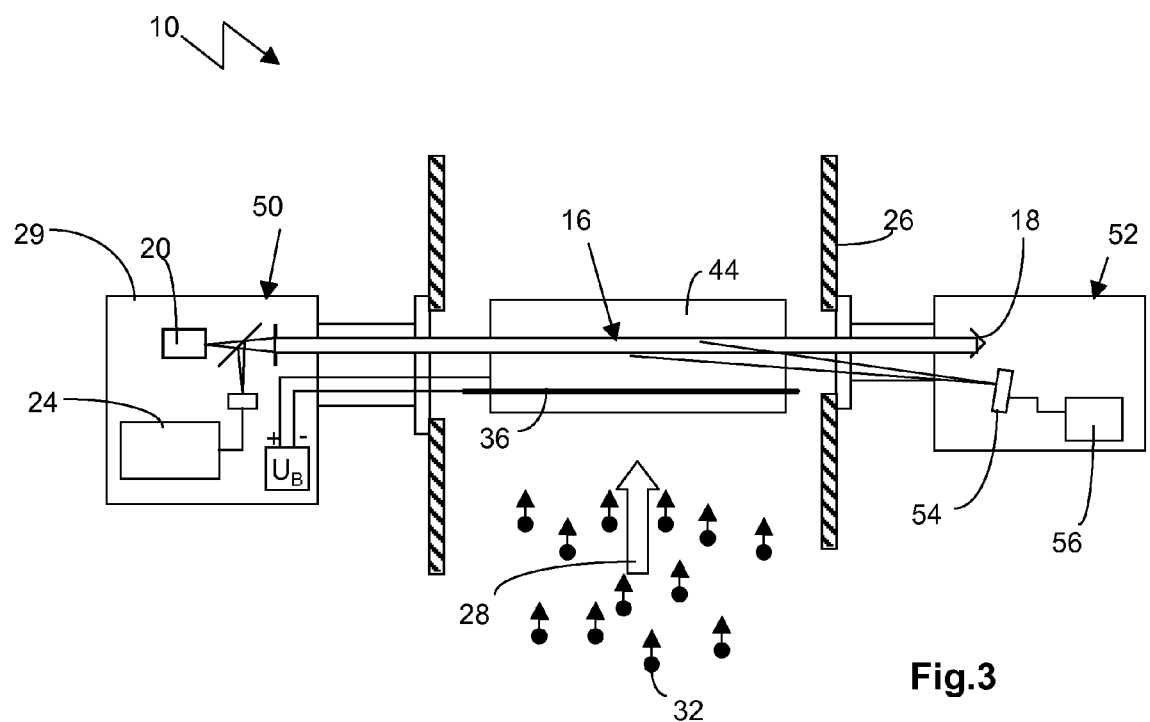
Figure 4:
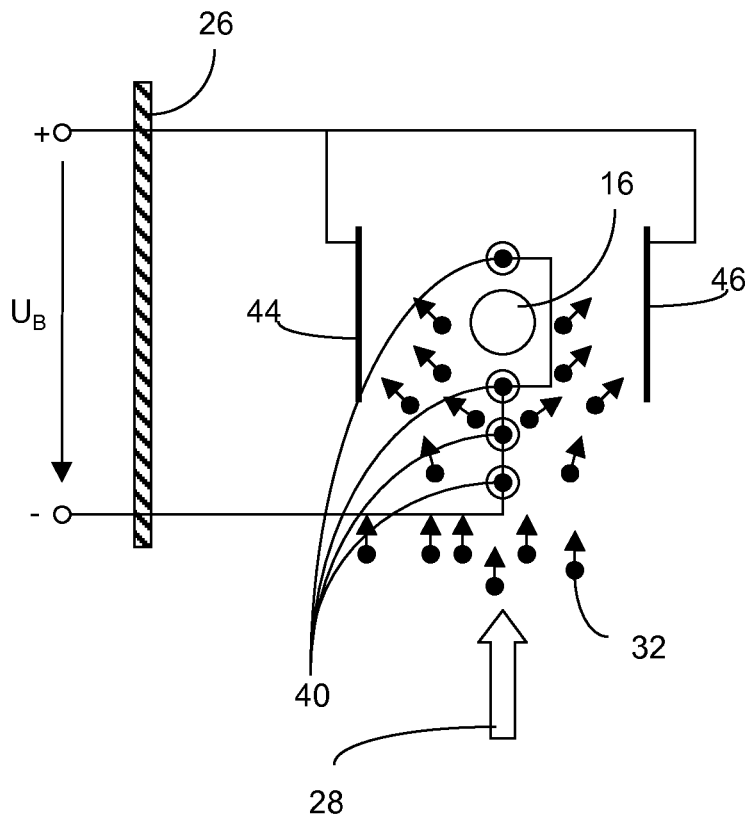
Figure 5:
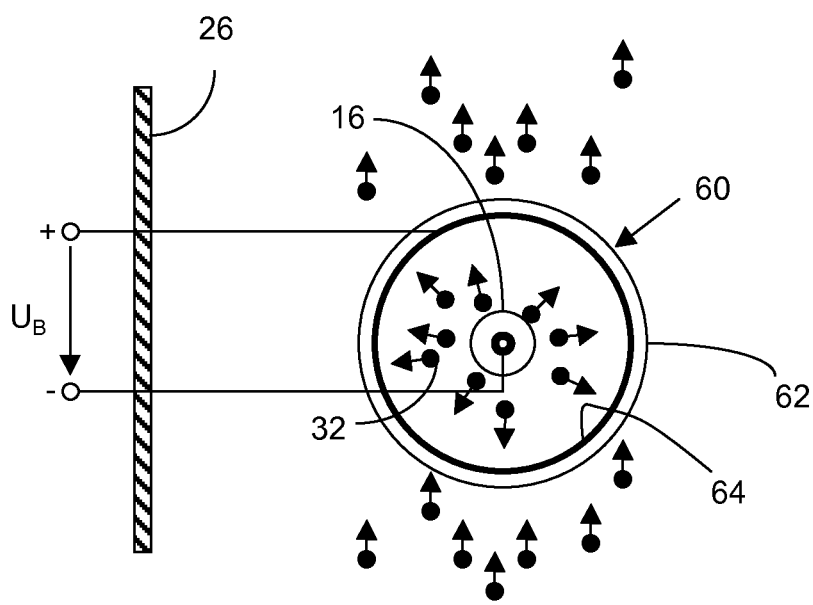

In the following the invention will be described in detail by means of embodiments with reference to the drawing. In the drawing there is shown:

FIG. 1 a schematic illustration of a first embodiment of the optoelectronic apparatus for gas analysis in a gas flow;

FIG. 2 the apparatus of FIG. 1 along the line I-I;

FIG. 3 a schematic illustration of a second embodiment;

FIGS. 4 and 5 illustrations like FIG. 2 of further embodiments.

An optoelectronic apparatus 10 in accordance with the invention for gas analysis in a gas flow 28 has a light transmitter 12 which transmits a transmission light beam 14 as is illustrated in a first embodiment in FIG. 1. The transmission light beam 14 defines a measurement volume 16 and is received by a light receiver 22 following the reflection at a retro-reflector 18 and a dividing mirror 20. The optical measurement path formed by the light beams 14 includes the measurement volume 16.

The light receiver 22 generates received signals in dependence on the incident light which are evaluated in an evaluation unit 24.

Such an optoelectronic apparatus 10 can, for example, be configured as a transmissiometer so that the intensity of the light passing through the measurement volume 16 can be measured by the light receiver 22. As a rule the light transmitter 12 is tuned to a certain wavelength which is absorbed by a gas constituent to be investigated, for example, hydrogen sulfide. A statement can then be made on how high the concentration of the interesting gas constituent is via the light received at the light receiver 22, for example, how high the concentration of hydrogen sulfide is in the gas flow 28 which is guided in a chimney 26.

The optoelectronic apparatus 10 includes a housing 29 having a lance-like extension 30, wherein the optoelectronic units, such as light transmitter 12, light receiver 22 and evaluation unit 24 are arranged in the housing 29 and the light is guided in the lance-like extension 30 through the measurement volume 16 and the retro-reflector 18 is held at the end of this extension 30. In this respect, the lance-like extension 30 naturally has openings in the region in which it projects into the chimney 26 so that the gas flow 28 can flow through the measurement volume 16.

The gas flow 28 guided in the chimney 26, which is merely indicated by an arrow 28, can be loaded with particles 32. These particles 32 can be dust, smoke or other aerosols, wherein the particles 32 interfere with the actual optical measurement in the measurement volume 16.

The apparatus 10 has an ionizer 36 and an ion acceleration apparatus 38 which are arranged in a specific way, to be able to deflect ions in the desired direction, to keep the particles 32 out of the measurement volume 16, i.e. to deflect them so much that they can, at least for the most part, flow past the measurement volume 16, wherein the flow direction of particles is indicated by the respective arrows 34.

The ionizer 36 in this embodiment comprises a discharge electrode 40 which is surrounded by an isolator 42. The discharge electrode 40 is also a part of the ion acceleration apparatus 38 which further has collector electrodes 44 and 46.

To deflect the particles 32 a high voltage $U_B$ is now applied between the discharge electrode 40 and the collector electrodes 44 and 46 which high voltage $U_B$ is supplied by a voltage source 47. A corona discharge is formed around the discharge electrode 40 which leads to the ionization of the particles 32 at a suitable high voltage $U_B$. The particles 32 charged thereby now experience a force in the direction of the electric field and thus a force in the direction of the collector electrode 44 or the collector electrode 46 which is arranged at least laterally beside the measurement volume 16. The discharge electrode 40 is itself arranged upstream in front of the measurement volume 16. As a result the particles 32 are thereby guided to the left and to the right past the measurement volume 16 as is shown in the illustration of FIG. 2. Other arrangements are plausible, wherein these must always be selected such that a force is exerted onto the ionized particles 32 to finally keep these particles away from the measurement volume, i.e. to guide the particle flow past the measurement volume.

A second embodiment of the optoelectronic apparatus 10 is illustrated in FIG. 3 in which the optoelectronic apparatus 10 is divided into two parts and has a first apparatus part 50 which is constructed like that of the first embodiment and a second apparatus part 52 which is arranged on the opposite side of the chimney 26 and in which the reflector 18 could, for example, be arranged. A second light receiver 54 can also be arranged in this second apparatus part 52 which is arranged such that it can, for example, receive scattered light so that an evaluation of the concentration of gas constituents can also take place on the basis of the principle of scattered light measurement with this measurement device 10. For this purpose the scattered light measured with the receiver 54 is evaluated in a second evaluation unit 56.

This embodiment also has an ionizer 36 and an ion acceleration apparatus 38 for deflecting the particles 32 around the measurement volume 16 like the first embodiment which are configured and arranged in a similar manner.

A large number of possibilities for the configuration of the ionizer 36 and the ion acceleration apparatus 38 exist. A further one of these possibilities is illustrated in FIG. 4, in which the ionizer 36 has a plurality of discharge electrodes 40, in this example has four discharge electrodes 40 of which three are arranged in the flow direction 28 in front of the measurement volume 16 and one is arranged behind the measurement volume 16. The collector electrodes 44 and 46 are in turn arranged laterally. Through the provision of a plurality of discharge electrodes 40 the probability for the ionization of the particles 32 should be increased so that the particles 32 can be deflected more efficiently.

Finally, FIG. 5 shows a further embodiment of the apparatus in accordance with the invention, in which the measurement volume 16 is surrounded by a mechanical filter 60 which is configured as a filter frit 62 in the present case. The filter frit 62 can, for example, be made of porous ceramic or of porous metal and can, for example, be arranged in the lance-like extension 30 of the first embodiment. Finest dust particles arrive in the measurement volume 16 by diffusion and interfere with the measurement there despite of the filter 60. The discharge electrode 40 is now arranged in the center of this cylinder symmetric arrangement of the filter 60, i.e. centrally in the measurement volume 16, to also keep the particles 32 out of the measurement volume 16. A collector electrode 64 is formed on the inner side of the filter 60 either by the filter 60 itself when this is composed of metal, or has a porous metal layer applied onto the inner side of the filter 60. Alternatively, a grid electrode (not illustrated) can also be provided on the filter inner surface.

As the gas only diffusely arrives in the inner space of the filter 60, the gas in the inner space is practically stationary. For this reason ionized particles 32 are accelerated out of the measurement volume in the direction of the collector electrode 64 and can no longer interfere with the optical measurement in the measurement volume 16.

The apparatus 10 in accordance with the invention works as follows:

The light transmitter 12 transmits the light beam 14 which penetrates the measurement volume present in the gas flow. A part of the light is absorbed in dependence on the gas constituents in the measurement volume and the remainder of the light is received by the light receiver 22 which generates received signals corresponding to the amount of light received. The received signals are evaluated in the evaluation unit 24 to finally obtain the concentration of an interested gas constituent.

To keep the disturbing particles 32 out of the measurement volume 16 the particles 32 are ionized by the ionizer 36 and the ionized particles 32 are deflected by the ion acceleration apparatus 38 composed of the discharge electrode 40 and the collector electrodes 44 and 46 and/or 62 so that, at least for the most part, they can flow past the measurement volume 16 and/or be kept out of the measurement volume 16.

In an improvement of this method in accordance with the invention the field strength can be modulated and the received signals can be evaluated under consideration of the modulation. The electric field applied to the ion acceleration apparatus must thus not necessarily be statically modulated, but can also be dynamically modulated, in particular be periodically modulated. The overall concentration of the particles in the medium can also be measured or at least be estimated via the evaluation of the received signals in dependence on the modulation for periodic modulation. Even a statement on the particle size distribution can be deduced from the received signal for a poly-disperse particle size distribution on a suitable selection of the modulation frequency, the modulation waveform and a sufficiently fine time resolution of the optical measurement channel. This is based on the fact that different sized particles have a different rate of mobility in the electric field and for this reason are accelerated out of the optical measurement volume or into the optical measurement volume to different degrees.

The invention claimed is:

1. An optoelectronic apparatus for optical gas analysis in a gas flow, having a light transmitter and a light receiver which define an optical measurement path including a measurement volume between one another, an evaluation unit, an ionizer which is arranged upstream of the optical measurement path, and an ion acceleration apparatus which is aligned such that the generated ions experience a deflection to away from the measurement volume.

2. An optoelectronic apparatus in accordance with claim 1, wherein the ionizer is configured as a discharge electrode of an electric filter and the ion acceleration apparatus is formed by the discharge electrode and a collector electrode of the electric filter.

3. An optoelectronic apparatus in accordance with claim 2, wherein the collector electrode is arranged at least laterally to the measurement volume when viewed in the flow direction.

4. An optoelectronic apparatus in accordance with claim 2, wherein a plurality of discharge electrodes are arranged upstream of the optical measurement path.

5. An optoelectronic apparatus for optical gas analysis, having a light transmitter and a light receiver which define an optical measurement path including a measurement volume between one another, an evaluation unit, an electric filter, wherein at least one discharge electrode of the electric filter is arranged in the volume which forms the optical measurement path and a collector electrode is arranged outside of the volume.

6. An apparatus in accordance with claim 5, wherein the electric filter is integrated into a mechanical filter, namely into a filter frit.

7. An apparatus in accordance with claim 5, wherein the discharge electrode is arranged centrally in the measurement volume, at least partially, and the collector electrode is arranged at the interior surfaces of the mechanical filter or is formed by the filter itself.

8. A method for optically analyzing a gas in a gas flow having the steps of: transmitting a light beam into a measurement volume penetrated the gas flow receiving the light beam with a receiver and generating received signals, evaluating the received signals, ionizing particles in the gas flow in an electric field and deflecting the ionized particles with the electric field so that they experience a deflection in a direction out of measurement volume so that they can flow past the measurement volume.

9. A method in accordance with claim 8, wherein the field strength is modulated and the received signals are evaluated under consideration of the modulation.

10. An optoelectronic apparatus for optical gas analysis in a gas flow, comprising:
a light transmitter and a light receiver, configured to receive incident light from the light transmitter, the light transmitter and light receiver defining an optical measurement path including a measurement volume between one another,
an evaluation unit,
an ionizer which is arranged upstream of the optical measurement path, and an ion acceleration apparatus which is aligned such that the generated ions experience a deflection to flow away from the measurement volume towards a collector electrode that collects the ions.

* * * * *